US00PP34025P3

(12) United States Plant Patent
Schoone

(10) Patent No.: US PP34,025 P3
(45) Date of Patent: Mar. 15, 2022

(54) ***PHALAENOPSIS* PLANT NAMED 'GOOD KARMA'**

(50) Latin Name: *Phalaenopsis hybrida*
Varietal Denomination: Good Karma

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,971

(22) Filed: Jun. 5, 2021

(65) Prior Publication Data

US 2021/0385995 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Good Karma', characterized by its upright plant habit; moderately vigorous to vigorous growth habit; strong flowering stems; strong leaves; freely flowering habit with typically two inflorescences per plant, each inflorescence with numerous flowers; large light purple-colored flowers with reddish purple-colored venation and stripes and white-colored margins; and good postproduction longevity.

2 Drawing Sheets

Figure 1:
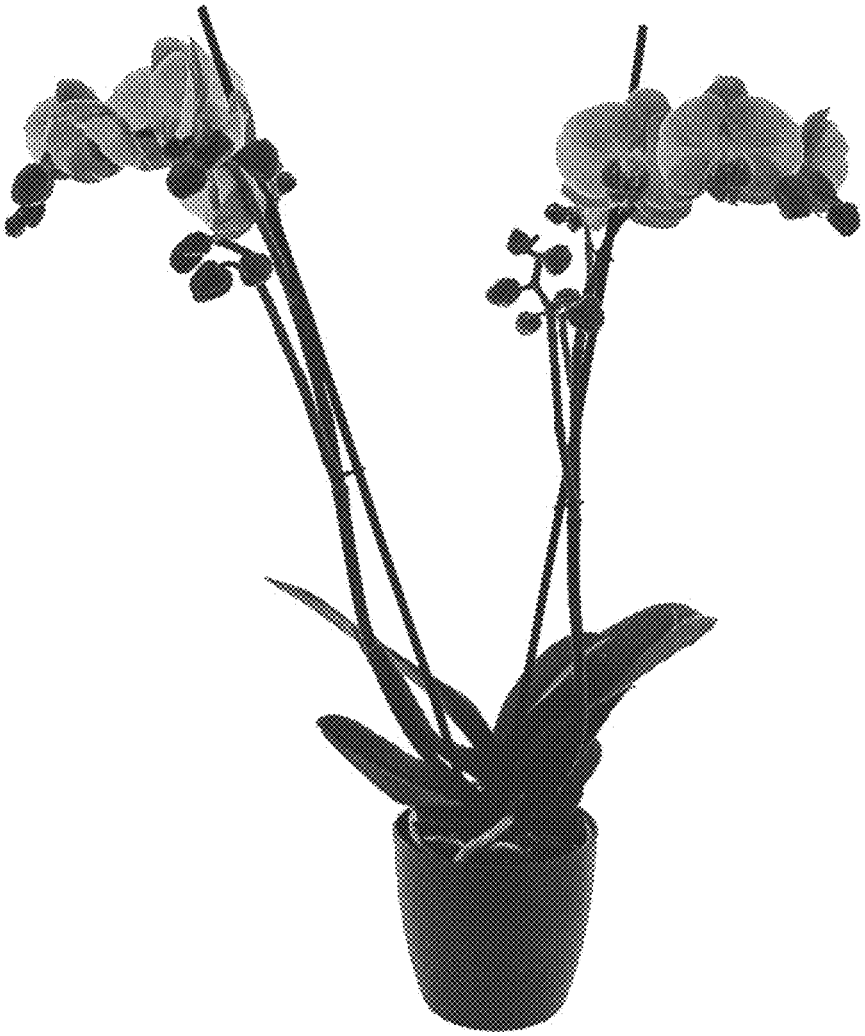

Botanical designation: *Phalaenopsis hybrida.*
Cultivar denomination: 'GOOD KARMA'.

CROSS-REFERENCED TO CLOSELY-RELATED APPLICATIONS

Title: Varieties of *Phalaenopsis* Plants
Inventor: René Schoone
Filed: Jun. 6, 2020
Ser. No. 62/705,003
Inventor and Applicant/Assignee hereby claims the benefit of this provisional U.S. Patent Application.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2187. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Good Karma'.

The new *Phalaenopsis* plant is a product of a planned breeding program conducted by the Inventor in Den Hoorn and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in January, 2011 in Den Hoorn, The Netherlands of a proprietary selection of *Phalaenopsis hybrida* identified as code number ST 4005, not patented, as the female, or seed, parent with a proprietary selection of *Phalaenopsis hybrida* identified as code number ST 3676, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in September, 2017.

Asexual reproduction of the new *Phalaenopsis* plant by in vitro meristem propagation in a controlled environment in Assendelft, The Netherlands since September, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Good Karma'. These characteristics in combination distinguish 'Good Karma' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences per plant, each inflorescence with numerous flowers.
6. Large light purple-colored flowers with reddish purple-colored venation and stripes and white-colored margins.
7. Good postproduction longevity.

Plants of the new *Phalaenopsis* can be compared to plants of the female parent selection. Plants of the new *Phalaenopsis* differ primarily from plants of the female parent selection in flower ground color as flowers of plants of the new *Phalaenopsis* are light purple in color whereas flowers of plants of the female parent selection are white in color. In addition, flowers of plants of the new *Phalaenopsis* have prominent venation and stripes whereas flowers of plants of the female parent selection are densely covered with spots and have no conspicuous venation and few stripes.

Plants of the new *Phalaenopsis* can be compared to plants of the male parent selection. Plants of the new *Phalaenopsis* differ primarily from plants of the male parent selection in flower ground color as flowers of plants of the new *Phalaenopsis* are light purple in color whereas flowers of plants of the male parent selection are violet in color. In addition, flowers of plants of the new *Phalaenopsis* have prominent venation and stripes whereas flowers of plants of the male parent selection have less conspicuous venation and fewer stripes.

Plants of the new *Phalaenopsis* can be compared to plants of *Phalaenopsis hybrida* 'Precious Love', disclosed in U.S. Provisional Patent application Ser. No. 62/705,003 and in a U.S. Plant patent application Ser. No. 17/339,962 filed concurrently. In side-by-side comparisons, plants of the new *Phalaenopsis* differ primarily from plants of 'Precious Love' in flower color as plants of the new *Phalaenopsis* have light purple-colored flowers with reddish purple-colored venation and stripes whereas plants of 'Precious Love' have purplish pink-colored flowers with darker purplish pink-colored stripes and venation.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Good Karma' grown in a container.

Figure 2:
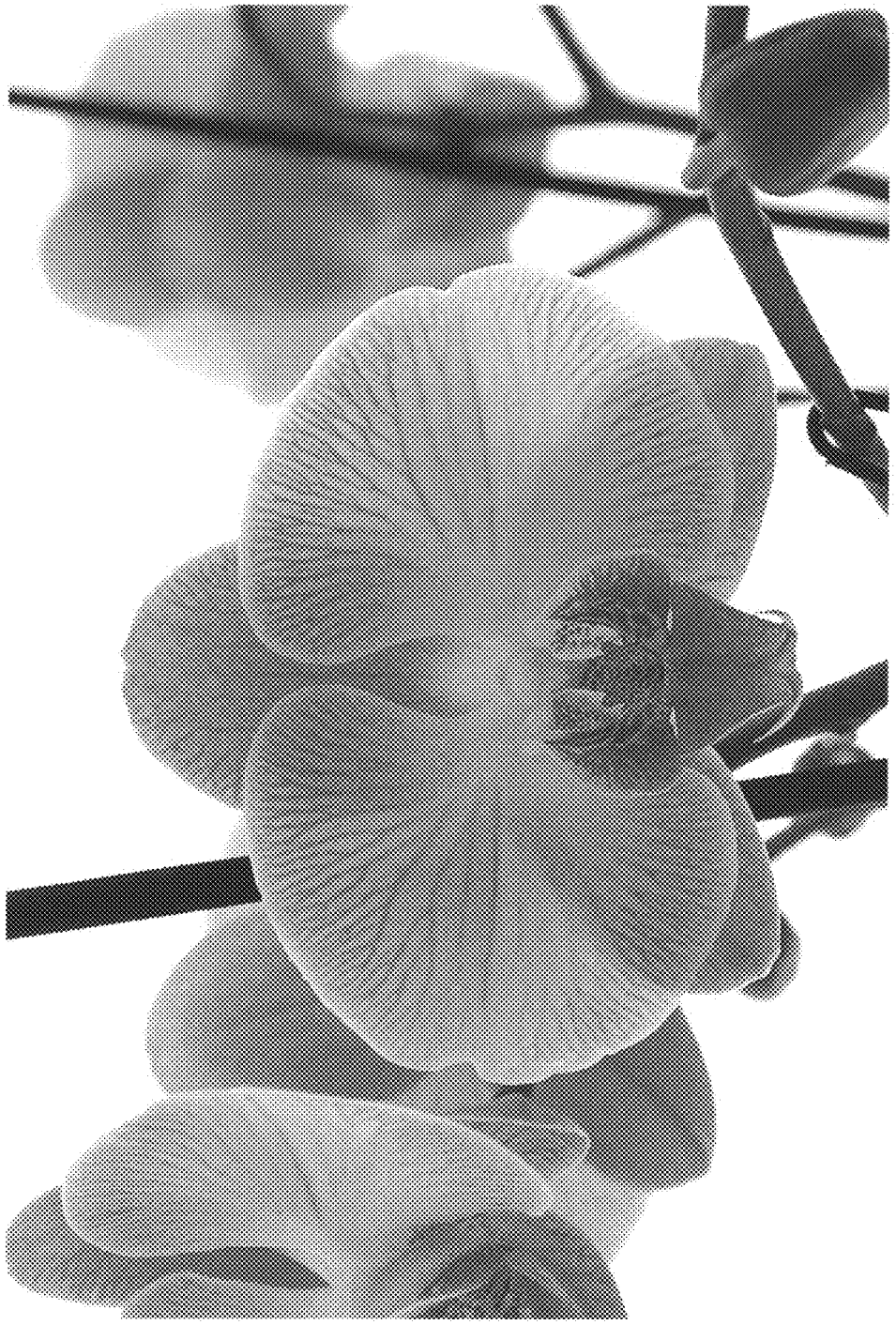

The photograph on the second sheet (FIG. 2) is a close-up view of a typical flower of 'Good Karma'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Good Karma'.

Parentage:

*Female parent*.—Proprietary selection of *Phalaenopsis hybrida* identified as code number ST 4005, not patented.

*Male parent*.—Proprietary selection of *Phalaenopsis hybrida* identified as code number ST 3676, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically grey to green in color; actual color of the roots is dependent on substrate composition, water quality, fertilizer, substrate temperature and age of roots.

*Rooting habit*.—Low amount of branching; medium density.

Plant description:

*Plant form and growth habit*.—Herbaceous epiphyte; upright plant habit with typically two inflorescences per plant, each inflorescence with numerous flowers; monopodial; moderately vigorous to vigorous growth habit and moderate growth rate.

*Plant height, substrate level to top of foliar plane*.—About 14.7 cm.

*Plant height, substrate level to top of inflorescences*.—About 48.4 cm.

*Plant diameter or spread*.—About 38 cm.

Leaf description:

*Arrangement and quantity*.—Distichous, simple; sessile; about seven leaves per plant.

*Length*.—About 18.5 cm.

*Width*.—About 6.2 cm.

*Aspect*.—Upright to outwardly arching.

*Shape*.—Oblanceolate to narrowly elliptic; slightly carinate.

*Apex*.—Unequal acute.

*Base*.—Sheathing. Sheath length: About 1.6 cm. Sheath width: About 1.7 cm. Sheath color: Close to 144A to 144B.

*Margin*.—Entire; slightly revolute.

*Texture and luster, upper and lower surfaces*.—Smooth, glabrous; slightly glossy.

*Venation pattern*.—Camptodromous.

*Color*.—Developing leaves, upper surface: Close to NN137A; margin edges, close to a blend of 143B and 144A. Developing leaves, lower surface: Close to 146A; margin edges, close to 144A. Fully expanded leaves, upper surface: Close to NN137B; margin edges, close to 143B; venation, close to NN137A. Fully expanded leaves, lower surface: Close to 146A; margin edges, close to 144A; venation, close to 143B.

Inflorescence description:

*Appearance and flowering habit*.—Showy zygomorphic flowers arranged on axillary branched racemes; typically two inflorescences per plant; each inflorescence with about 21 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 33 cm.

*Inflorescence width*.—About 22.5 cm.

*Flower buds*.—Height: About 2.2 cm. Diameter: About 1.7 cm by 2.1 cm. Shape: Broadly ovate. Color: Close to a blend of 176B and 182B; proximally, close to 183C.

*Flower size*.—Large, about 7.3 cm (vertical) by 8.9 cm (horizontal).

*Flower depth*.—About 3.1 cm.

*Petals, quantity and arrangement*.—Three, two lateral petals and one center petal transformed into a labellum.

*Lateral petals*.—Length: About 4.2 cm. Width: About 5.5 cm. Shape: Reniform to lunate. Apex: Obtuse. Margin: Entire. Texture and luster, upper and lower surfaces: Smooth, glabrous, velvety; matte. Color: When opening, upper surface: Distally, close to 76B and proximally, close to 76C; margin edges, close to NN155D; towards the base, close to NN155D; venation, close to N78B. When opening, lower surface: Distally, close to N75D and proximally, close to 76D; margin edges, close to NN155D; towards the base, close to NN155B; venation, distally, close to N78C and proximally, close to N75B. Fully opened, upper surface: Distally, close to between 76A and 76B and proximally, close to a blend of 76D and NN155C; margin edges, close to NN155D; towards the base, close to NN155D; venation, close to N78B; color does not change with subsequent development. Fully opened, lower surface: Distally, close to between 76A and 76B and proximally, close to a blend of 60D and NN155C; margin edges, close to NN155D; towards the base, close to NN155B; venation, distally, close to N78C to N78D and proximally, close to N78D to lighter than N78D; color does not change with subsequent development.

*Labella*.—Appearance: Three-parted with two lateral lobes and a central lobe. Length, lateral lobes: About 2.1 cm. Width, lateral lobes: About 1.7 cm. Length, central lobe: About 3.3 cm. Width, central lobe: About 9 mm to 21 mm. Shape, lateral lobes: Obovate. Shape, central lobe: Deltoid. Apex, lateral lobes: Rounded. Apex, central lobe: Cleft with two narrow and recurved cirrose tips, about 1.1 cm in length and about 1.1 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 7 mm in width and about 6 mm in height. Color: When opening, upper surface: Lateral lobes: Close to NN155B; distally, tinged with close to lighter than 76D with dense venation, close to 71C; proximally, close to 22B and at the base, blotches and stripes, close to 184B and 184C. Central lobe: Close to 59D; towards the margins and apex, strongly tinged with close to 164B; margin edges, close to NN155D; venation, close to 64B and 64C; at the base (at column connection), close to NN155D with radial stripes, close to 176A; cirrose tips, close to 64B with margin edges, close to NN155D. Callosities: Close to 11B; fine dots, close to 176B and 176C. When opening, lower surface: Lateral lobes: Close to 156D; basal margin, close to 18A; venation, close to 64A and 64B. Central lobe: Close to N155B; towards the margins and apex, strongly tinged with close to 165B with venation, close to 70B; towards the base, close to 182B to 182C and at the base (at column connection), close to 157B. Fully opened, upper surface: Lateral lobes: Close to NN155B; distally, tinged with close to lighter than 76D with dense venation, close to 71C; proximally, close to 22B and at the base, blotches and stripes, close to 184B and 184C. Central lobe: Close to 59D; towards the margins and apex, strongly tinged with close to 161A; margin edges, close to NN155D; venation, close to 64B and 64C; at the base (at column connection), close to NN155D with radial stripes, close to 176A; cirrose tips, close to 64B with margin edges, close to NN155D. Callosities: Close to 11A to 11B; fine dots, close to 176B and 176C. Fully opened, lower surface: Lateral lobes: Close to 156D; basal margin, close to 162A; venation, close to 64A and 64B. Central lobe: Close to N155B; towards the margins and apex, strongly tinged with close to 165B with venation, close to 70B; towards the base, close to 182B to 182C and at the base (at column connection), close to 157B.

*Sepals*.—Quantity and arrangement: Three, one upper dorsal sepal and two lower lateral sepals. Length, dorsal sepal: About 4.4 cm. Width, dorsal sepal:

About 3.3 cm. Length, lateral sepals: About 4.4 cm. Width, lateral sepals: About 2.8 cm. Shape, dorsal sepal: Obovate to elliptic. Shape, lateral sepals: Ovate. Apex, dorsal sepal: Shallowly retuse. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to N78C; towards the apex, close to 76A to 76B; towards the base, close to NN155B; margin edges, close to NN155D; venation, close to N78A and N78B. When opening, lower surface: Close to a blend of close to N77B and 186B; center, tinged with close to 197C; towards the margins, close to 77C; venation, close to N78B. Fully opened, upper surface: Close to N78C and N78D; towards the apex, close to 77D; towards the base, close to NN155C; margin edges, close to 76D; venation, close to a blend of N78B and NN78A. Fully opened, lower surface: Close to a blend of 77B and 77C; center, tinged with close to 197C; venation at margins, close to N78B. Color, lateral sepals: When opening, upper surface: Close to 156A and 156B; towards the margins and apex, close to 76A with venation, close to N78B; towards the base, close to 145C and at the base, fine dots, close to N186D. When opening, lower surface: Close to 70B and N77B; towards the base, tinged with close to 197B; venation, close to a 178A. Fully opened, upper surface: Close to N75C; towards the margins and apex, close to N75B with venation, close to N78B; towards the base, close to 145D and at the base, fine dots, close to N186D. Fully opened, lower surface: Close to a blend of 77B and N77B; towards the base, close to a blend of N75A and 77C; venation, close to a 182B.

*Peduncles*.—Length: About 54.4 cm. Diameter: About 7 mm. Strength: Strong. Aspect: Upright to outwardly arching. Texture and luster: Smooth, glabrous; matte. Color: Close to 138A; densely covered with fine dots, proximally, close to N189A and distally, close to 147A.

*Pedicels*.—Length: About 3 cm. Diameter: About 3 mm. Strength: Moderately strong. Aspect: About 60° from peduncle axis. Texture and luster: Smooth, glabrous; matte. Color: Close to 146D; proximally, close 148A and distally, close to 196C.

*Reproductive organs*.—Androecium: Column length: About 9 mm. Column width: About 6.5 mm. Column color: Close to NN155B; faint blotch, close to 76A. Pollinia quantity: Two. Pollinia diameter (per two pollinia): About 3 mm. Pollinia color: Close to N25B. Gynoecium: Stigma length: About 3 mm. Stigma width: About 5 mm. Stigma shape: Reniform. Stigma color: Close to 157D. Ovary length: About 8 mm. Ovary diameter: About 1 mm. Ovary color: Close to 145A. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Good Karma' as illustrated and described.

* * * * *